United States Patent
Elkarim Albadri et al.

(10) Patent No.: US 12,092,580 B1
(45) Date of Patent: Sep. 17, 2024

(54) **MULTIVARIATE OPTIMIZATION OF MICROWAVE DIGESTION FOR DETERMINING OF SOME ELEMENTS IN BAOBAB (*A. DIGITATA* L.) FRUIT PULP BY ICP-MS**

(71) Applicant: KING FAISAL UNIVERSITY, Al-Ahsa (SA)

(72) Inventors: Abuzer Ebead Awad Elkarim Albadri, Al-Ahsa (SA); Abdalla Ahmed Elbashir, Al-Ahsa (SA); Ahmed O. Anlajjar, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/418,151

(22) Filed: Jan. 19, 2024

(51) Int. Cl.
*G01N 33/02* (2006.01)
*G01N 1/28* (2006.01)
*G01N 1/38* (2006.01)
*G01N 1/40* (2006.01)
(Continued)

(52) U.S. Cl.
CPC ............. *G01N 21/73* (2013.01); *G01N 1/286* (2013.01); *G01N 1/38* (2013.01); *G01N 1/4077* (2013.01); *G01N 1/44* (2013.01); *G01N 33/025* (2013.01); *G01N 2001/2866* (2013.01); *G01N 2001/4088* (2013.01); *Y10T 436/24* (2015.01);
(Continued)

(58) Field of Classification Search
CPC .......... G01N 21/73; G01N 1/286; G01N 1/38; G01N 1/4077; G01N 1/44; G01N 33/02; G01N 33/025; G01N 2001/2866; G01N 2001/4088; Y10T 436/24; Y10T 436/25; Y10T 436/25125; Y10T 436/25375; Y10T 436/25625

USPC ......... 436/20, 147, 157, 173, 174, 175, 177, 436/179
See application file for complete search history.

(56) References Cited

U.S. PATENT DOCUMENTS

2017/0151151 A1   6/2017   Banowski et al.

FOREIGN PATENT DOCUMENTS

WO   2015035532 A1   3/2015

OTHER PUBLICATIONS

Ramakrishna et al. Annals of Phytomedicine, vol. 8(2), Dec. 30, 2019, pp. 127-133.*
(Continued)

*Primary Examiner* — Maureen Wallenhorst
(74) *Attorney, Agent, or Firm* — Nath, Goldberg & Meyer; Joshua B. Goldberg (57) ABSTRACT

A method of measuring a plurality of chemical elements in a baobab fruit pulp can include crushing and homogenizing baobab fruit pulp; sieving the homogenized baobab fruit pulp to obtain baobab fruit fine powder; adding the baobab fruit fine powder to each of prepared plurality of acid mixtures to obtain a plurality of solutions; heating each of the plurality of solutions to digest the baobab fruit fine powder in each of the plurality of solutions; cooling the plurality of solutions; filtering the digested baobab fruit fine powder from each of the plurality of solutions to obtain a plurality of filtered digested baobab fruit fine powders; diluting each of the plurality of filtered digested baobab fruit fine powders with water to obtain a plurality of mixtures; and measuring the plurality of chemical elements in each of the plurality of mixtures using inductively coupled plasma mass spectrometry (ICP-MS).

14 Claims, 1 Drawing Sheet

(51) Int. Cl.
    *G01N 1/44*         (2006.01)
    *G01N 21/73*      (2006.01)

(52) U.S. Cl.
    CPC ............... *Y10T 436/25125* (2015.01); *Y10T 436/25375* (2015.01); *Y10T 436/25625* (2015.01)

(56) References Cited

OTHER PUBLICATIONS

Ebrahim et al. Journal of Natural Medicine, vol. 66, Feb. 12, 2012, pp. 671-679.*

Sibiya et al. South African Journal of Botany, vol. 132, May 23, 2020, pp. 87-94.*

Dos Anjos et al. Talanta, vol. 178, Oct. 7, 2017, pp. 842-846.*

Novaes et al. Current Analytical Chemistry, vol. 12, 2016, pp. 94-101.*

Jiang et al. Molecules, vol. 19, Apr. 10, 2014, pp. 4452-4465.*

Debelo H, Ndiaye C, Kruger J, Hamaker BR, Ferruzzi MG. "African Adansonia digitata fruit pulp (baobab) modifies provitamin A carotenoid bioaccessibility from composite pearl millet porridges", J Food Sci Technol. Apr. 2020;57(4):1382-1392.

Rehman, Rabia. "Toxic and Nutritive Elements Analysis of Commercially Available Tea Samples of Pakistan by Icpoes Employing Microwave Digestion." Electronic Journal of Environmental, Agricultural and Food Chemistry (EJEAFChe) 11.05 (2011): 459-468.

Khoja, Kholoud K., et al. "In vitro bioaccessibility and bioavailability of iron from fenugreek, baobab and moringa", Food Chemistry 335 (2021): 127671.

N.P. Sibiya, E. Kayitesi, A. Moteetee, "Mineral composition of selected indigenous wild southern African fruits", South African Journal of Botany, vol. 132, 2020, pp. 87-94.

Coe SA, Clegg M, Armengol M, Ryan L. "The polyphenol-rich baobab fruit (*Adansonia digitata* L.) reduces starch digestion and glycemic response in humans", Nutr. Res. Nov. 2013;33(11):888-96.

Oliveira, Andrea, Nivaldo Baccan, and Solange Cadore. "Evaluation of metal ions in rice samples: extraction and direct determination by ICP OES." Journal of the Brazilian Chemical Society 23 (2012): 838-845.

\* cited by examiner

MULTIVARIATE OPTIMIZATION OF MICROWAVE DIGESTION FOR DETERMINING OF SOME ELEMENTS IN BAOBAB (*A. DIGITATA* L.) FRUIT PULP BY ICP-MS

FIELD AND BACKGROUND

The disclosure of the present application relates to a method of measuring a plurality of chemical elements in a baobab fruit pulp.

DESCRIPTION OF THE PRIOR ART

*Adansonia digitata*, commonly called baobab, is a tree plant belonging to the Malvaceae family and can be found in several countries including Africa and Asia. The flowers of the baobab tree open for one night and are usually pollinated by fruit bats. The baobab fruits, resulting from the pollination, are oval shaped and contain seeds surrounded by a chalky pulp rich in vitamins and minerals.

The chalky pulp is high in fiber, vitamin C, vitamin B, antioxidants, potassium, magnesium, iron, sodium, phosphorous, calcium, zinc, and other minerals. The seeds are loaded with a high level of vitamins, minerals, amino acids, fatty acids, antioxidants, and polyphenols. Baobab fruit has about 7-10 times more vitamin C than oranges, about 5 times more magnesium than avocados, about 6 times more potassium than bananas, and about 2 times more calcium than milk from a cow. The fruit is also rich in thiamine, and lysine.

Due to its nutritional values, rural communities consume the seeds and pulp of the baobab fruit as food sources. The pulp is consumed by pregnant women and young children for its calcium content. The pulp of the baobab fruit is usually used in the preparation of fruit juices, snacks, sweets, porridges, and food recipes. Across the globe, many countries are using the baobab fruit pulp for applications in food and beverages, nutraceuticals, personal care, and others.

Despite the high richness in vitamins and minerals of baobab fruit pulp, nutritional composition of the baobab fruit pulp has not been fully investigated. Due to this deficiency, full potential of baobab fruit pulp cannot be achieved.

Thus, a method of measuring a plurality of chemical elements in a baobab fruit pulp is needed.

SUMMARY

The present subject matter relates to a method of measuring a plurality of chemical elements in a baobab fruit pulp. The present subject matter further relates to a method of optimizing microwave digestion, a method of using the optimized microwaved digestion to perform microwave digestion, and a method of determining accuracy of response surface methodology (Box-Behnken design).

In one embodiment, the method of measuring a plurality of chemical elements in a baobab fruit pulp includes obtaining pulp from a baobab fruit; crushing and homogenizing the baobab fruit pulp to obtain a homogenized baobab fruit pulp; sieving the homogenized baobab fruit pulp to obtain baobab fruit fine powder; preparing a plurality of acid mixtures; adding the baobab fruit fine powder to each of the prepared plurality of acid mixtures to obtain a plurality of solutions; heating each of the plurality of solutions to digest the baobab fruit fine powder in each of the plurality of solutions to obtain a digested baobab fruit fine powder in each of the plurality of solutions; cooling the plurality of solutions; filtering the digested baobab fruit fine powder from each of the plurality of solutions to obtain a plurality of filtered digested baobab fruit fine powders; diluting each of the plurality of filtered digested baobab fruit fine powders with water to obtain a plurality of mixtures; and measuring the plurality of chemical elements in each of the plurality of mixtures using inductively coupled plasma mass spectrometry (ICP-MS).

In an embodiment, the homogenized baobab fruit pulp can be prepared by crushing and homogenizing the baobab fruit pulp with an agate mortar and pestle.

In an embodiment, the plurality of acid mixtures can have 12 acid mixtures each respectively can have:a) about 3 mL of nitric acid ($HNO_3$), b) about 5 mL of $HNO_3$, c) about 7 mL of $HNO_3$, d) about 7 mL of $HNO_3$:water ($H_2O$) (1:3), e) about 7 mL of $HNO_3$:$H_2O$ (1:1), f) about 7 mL of $HNO_3$:$H_2O$ (3:1), g) about 7 mL of $HNO_3$:$H_2O$ (1:1):about 2 mL of hydrogen peroxide ($H_2O_2$), h) about 7 mL of $HNO_3$:$H_2O$ (1:1):about 4 mL of $H_2O_2$, i) about 7 mL of $HNO_3$:$H_2O$ (1:1):about 6 mL of $H_2O_2$, j) about 3 mL of $HNO_3$:about 4 mL of $H_2O_2$, k) about 5 mL of $HNO_3$:about 4 mL of $H_2O_2$, and l) about 7 mL of $HNO_3$:about 4 mL of $H_2O_2$.

In another embodiment, the plurality of solutions can be prepared by adding about 0.4 g of the baobab fruit fine powder to each of the prepared plurality of acid mixtures within a plurality of vessels.

In another embodiment, the digested baobab fruit fine powder in each of the plurality of solutions within each of the plurality of vessels can be prepared by sealing each of the plurality of vessels and heating the plurality of solutions to digest the baobab fruit fine powder in each of the plurality of solutions within each of the sealed plurality of vessels in an oven cavity of a microwave digestion at about 100° C. for about 5 minutes, then at about 130° C. for about 15 minutes, and thereafter cooling each of the plurality of solutions within each of the sealed plurality of vessels.

In an embodiment, the plurality of chemical elements can be selected from the group consisting of sodium, magnesium, aluminum, potassium, calcium, vanadium, chromium, manganese, cobalt, copper, selenium, barium, other chemical elements, and combinations thereof.

In a further embodiment, the present subject matter relates to a method of optimizing microwave digestion, the method includes normalizing the measured plurality of chemical elements in each of the plurality of mixtures obtained by the method above to obtain a plurality of normalized measured chemical elements values; generating a plurality of run data by incorporating the plurality of normalized measured chemical elements values and microwave digestion factor variables into a response surface methodology (Box-Behnken design) to obtain multiple response (MR) values and concentration values for each of the plurality of normalized measured chemical elements; determining which run data generated a highest multiple response value and highest concentration values for each of the plurality of normalized measured chemical elements; and detecting which of the plurality of acid mixtures obtained by the method above correspond with the determined run data to obtain optimized microwave digestion.

In an embodiment, each of the plurality of normalized measured chemical elements values can be prepared by dividing the chemical element concentration measured for each of the measured plurality of chemical elements in each of the plurality of mixtures by a highest concentration of the same chemical element measured for each of the measured plurality of chemical elements in each of the plurality of mixtures.

In another embodiment, the multiple response values and concentration values for each of the plurality of normalized measured chemical elements can be prepared by generating a plurality of run data by incorporating the plurality of normalized measured chemical elements values and microwave digestion factor variables into a response surface methodology (Box-Behnken design) comprising about 27 factorial experiments with about 3 center points, and wherein the microwave digestion factor variables can have a microwave temperature of about 125° C., an acid mixture volume of about 10 mL, a sample weight of about 0.1 g, and a radiation time of about 15 minutes.

In a further embodiment, the present subject matter relates to a method of performing microwave digestion, the method includes obtaining pulp from a baobab fruit; crushing and homogenizing the baobab fruit pulp to obtain a homogenized baobab fruit pulp; sieving the homogenized baobab fruit pulp to obtain baobab fruit fine powder; preparing the detected acid mixture obtained by the method above; adding the baobab fruit fine powder to the detected acid mixture to obtain a solution; heating the solution to digest the baobab fruit fine powder in the solution to obtain a digested baobab fruit fine powder in the solution; cooling the solution; filtering the digested baobab fruit fine powder from the solution to obtain a filtered digested baobab fruit fine powder; diluting the filtered digested baobab fruit fine powder with water to obtain a mixture; and measuring the mixture using inductively coupled plasma mass spectrometry (ICP-MS).

In an embodiment, the detected acid mixture can have about 7 mL of $HNO_3:H_2O$ (1:1):about 2 mL of hydrogen peroxide ($H_2O_2$).

In an embodiment, the solution can be prepared by adding about 0.1 g of the baobab fruit fine powder to the prepared detected acid mixture within a vessel.

In an embodiment, the digested baobab fruit fine powder in the solution within the vessel can be prepared by sealing the vessel and heating the solution to digest the baobab fruit fine powder in the solution within the sealed vessel in an oven cavity of a microwave digestion at about 100° C. for about 5 minutes then at about 130° C. for about 15 minutes and thereafter cooling the solution within the sealed vessel.

In an embodiment, the plurality of chemical elements can be selected from the group consisting of sodium, magnesium, aluminum, potassium, calcium, vanadium, chromium, manganese, cobalt, copper, selenium, barium, other chemical elements, and combinations thereof.

In another embodiment, the water can be deionized water.

In a further embodiment, the present subject matter relates a method of determining accuracy of response surface methodology (Box-Behnken design), the method includes obtaining a baobab fruit; preparing an analyte solution; adding the analyte solution at various concentrations to the baobab fruit; and determining recovery rates (R) for each chemical elements in the baobab fruit.

In an embodiment, the analyte solution can be selected from the group consisting of barium, sodium, magnesium, aluminum, potassium, calcium, vanadium, chromium, manganese, cobalt, copper, zinc, iron, and selenium, other chemical elements, and combinations thereof.

In an embodiment, the various concentrations of the analyte solution can have about 25 ug/L, about 50 ug/L, and about 100 ug/L.

These and other features of the present subject matter will become readily apparent upon further review of the following specification.

DETAILED DESCRIPTION

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method of measuring a plurality of chemical elements in a baobab fruit pulp. The present subject matter further relates to a method of optimizing microwave digestion, a method of using the optimized microwaved digestion to perform microwave digestion, and a method of determining accuracy of response surface methodology (Box-Behnken design).

Figure 1:
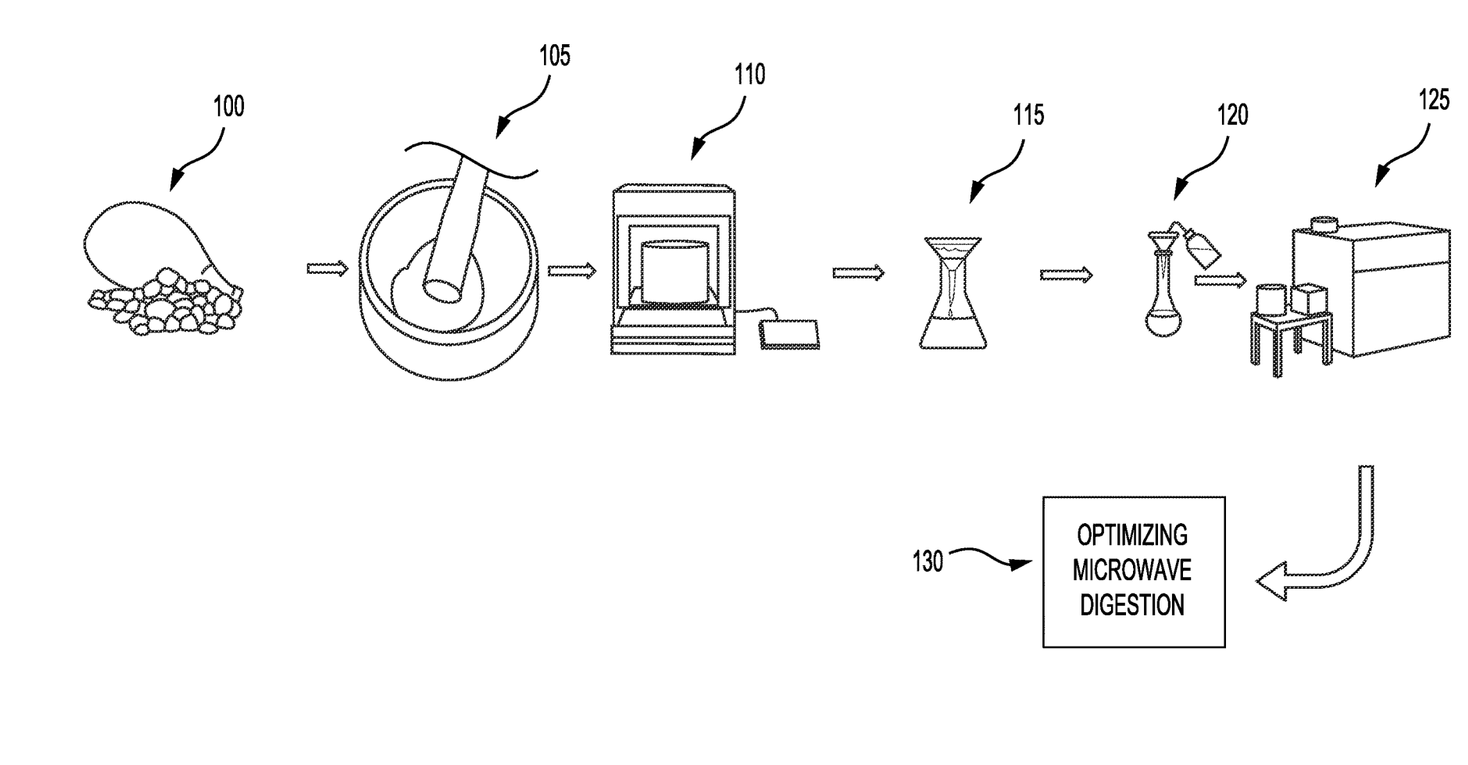
FIG. 1 depicts the processes for measuring a plurality of chemical elements in a baobab fruit pulp, optimizing microwave digestion, and performing microwave digestion.

FIG. 1 depicts, in one embodiment, a method of measuring a plurality of chemical elements in a baobab fruit pulp which includes obtaining pulp from a baobab fruit in step (100); crushing and homogenizing the baobab fruit pulp to obtain a homogenized baobab fruit pulp in step (105); sieving the homogenized baobab fruit pulp to obtain baobab fruit fine powder (not shown); preparing a plurality of acid mixtures (not shown); adding the baobab fruit fine powder to each of the prepared plurality of acid mixtures to obtain a plurality of solutions (not shown); heating each of the plurality of solutions to digest the baobab fruit fine powder in each of the plurality of solutions to obtain a digested baobab fruit fine powder in each of the plurality of solutions in step (110); cooling the plurality of solutions in step (110); filtering the digested baobab fruit fine powder from each of the plurality of solutions to obtain a plurality of filtered digested baobab fruit fine powders in step (115); diluting each of the plurality of filtered digested baobab fruit fine powders with water to obtain a plurality of mixtures in step (120); and measuring the plurality of chemical elements in each of the plurality of mixtures using inductively coupled plasma mass spectrometry (ICP-MS) in step (125).

In an embodiment, the method can include manually separating pulp from the seed of the baobab fruit. Afterward, the baobab fruit pulp can be crushed and homogenized using an agate mortar and pestle to obtain a homogenized baobab fruit pulp. Then, the homogenized baobab fruit pulp can be placed in a plastic sieve with 1 mm pores to obtain baobab fruit fine powder.

In an embodiment, a plurality of acid mixtures can be prepared. The plurality of acid mixtures can have 12 acid mixtures each respectively can have:a) about 3 mL of nitric acid ($HNO_3$), b) about 5 mL of $HNO_3$, c) about 7 mL of $HNO_3$, d) about 7 mL of $HNO_3$:water ($H_2O$) (1:3), e) about 7 mL of $HNO_3$:$H_2O$ (1:1), f) about 7 mL of $HNO_3$:$H_2O$ (3:1), g) about 7 mL of $HNO_3$:$H_2O$ (1:1):about 2 mL of hydrogen peroxide ($H_2O_2$), h) about 7 mL of $HNO_3$:$H_2O$ (1:1):about 4 mL of $H_2O_2$, i) about 7 mL of $HNO_3$:$H_2O$ (1:1):about 6 mL of $H_2O_2$, j) about 3 mL of $HNO_3$:about 4 mL of $H_2O_2$, k) about 5 mL of $HNO_3$:about 4 mL of $H_2O_2$, and 1) about 7 mL of $HNO_3$:about 4 mL of $H_2O_2$.

In an embodiment, about 0.4 g of the baobab fruit fine powder can be added to each of the prepared plurality of acid mixtures within a plurality of vessels to obtain a plurality of solutions with the plurality of vessels.

In an embodiment, each of the plurality of vessels can be sealed and the plurality of solutions can be heated to digest the baobab fruit fine powder in each of the plurality of solutions within each of the sealed plurality of vessels in an oven cavity of a microwave digestion at about 100° C. for about 5 minutes, then at about 130° C. for about 15 minutes, and thereafter cooling each of the plurality of solutions within each of the sealed plurality of vessels to obtain a digested baobab fruit fine powder in each of the plurality of solutions within each of the sealed plurality of vessels.

In an embodiment, the digested baobab fruit fine powder can be filtered from each of the plurality of solutions to obtain a plurality of filtered digested baobab fruit fine powders. Afterward, each of the plurality of filtered digested baobab fruit fine powders can be diluted with about 100 mL of deionized water to obtain a plurality of mixtures.

In an embodiment, the plurality of chemical elements in each of the plurality of mixtures can be measured using inductively coupled plasma mass spectrometry (ICP-MS). The plurality of chemical elements can be selected from the group consisting of sodium, magnesium, aluminum, potassium, calcium, vanadium, chromium, manganese, cobalt, copper, selenium, barium, other chemical elements, and combinations thereof.

In a further embodiment, the present subject matter relates to a method of optimizing microwave digestion in step (130) as shown in FIG. 1, the method includes normalizing the measured plurality of chemical elements in each of the plurality of mixtures obtained by the method above to obtain a plurality of normalized measured chemical elements values; generating a plurality of run data by incorporating the plurality of normalized measured chemical elements values and microwave digestion factor variables into a response surface methodology (Box-Behnken design) to obtain multiple response (MR) values and concentration values for each of the plurality of normalized measured chemical elements; determining which run data generated a highest multiple response value and highest concentration values for each of the plurality of normalized measured chemical elements; and detecting which of the plurality of acid mixtures obtained by the method above correspond with the determined run data to obtain optimized microwave digestion.

In one embodiment, the method of optimizing microwave digestion can include normalizing the measured plurality of chemical elements in each of the plurality of mixtures obtained by the method above to obtain a plurality of normalized measured chemical elements values. Each of the plurality of normalized measured chemical elements values can be prepared by dividing the chemical element concentration measured for each of the measured plurality of chemical elements in each of the plurality of mixtures by a highest concentration of the same chemical element measured for each of the measured plurality of chemical elements in each of the plurality of mixtures.

In an embodiment, the plurality of normalized measured chemical elements values and microwave digestion factor variables can be incorporated into a response surface methodology (Box-Behnken design) to generate a plurality of run data to obtain multiple response (MR) values and concentration values for each of the plurality of normalized measured chemical elements. The response surface methodology (Box-Behnken design) can have about 27 factorial experiments with about 3 center points using a Minitab software. The microwave digestion factor variables can have a microwave temperature of about 125° C., an acid mixture volume of about 10 mL, a sample weight of about 0.1 g, and a radiation time of about 15 minutes.

In a further embodiment, the present subject matter relates to a method of performing microwave digestion as shown in FIG. 1, the method includes obtaining pulp from a baobab fruit in step (100); crushing and homogenizing the baobab fruit pulp to obtain a homogenized baobab fruit pulp in step (105); sieving the homogenized baobab fruit pulp to obtain baobab fruit fine powder (not shown); preparing the detected acid mixture obtained by the method above (not shown); adding the baobab fruit fine powder to the detected acid mixture to obtain a solution (not shown); heating the solution to digest the baobab fruit fine powder in the solution to obtain a digested baobab fruit fine powder in the solution in step (110); cooling the solution in step (110); filtering the digested baobab fruit fine powder from the solution to obtain a filtered digested baobab fruit fine powder in step (115); diluting the filtered digested baobab fruit fine powder with water to obtain a mixture in step (120); and measuring the mixture using inductively coupled plasma mass spectrometry (ICP-MS) in step (125).

In one embodiment, the method of performing microwave digestion can include manually separating pulp from the seed of the baobab fruit. Afterward, the baobab fruit pulp can be crushed and homogenized using an agate mortar and pestle to obtain a homogenized baobab fruit pulp. Then, the homogenized baobab fruit pulp can be placed in a plastic sieve with 1 mm pores to obtain baobab fruit fine powder.

In an embodiment, the detected acid mixture obtained by the method above can be prepared. The detected acid mixture can have about 7 mL of $HNO_3:H_2O$ (1:1):about 2 mL of hydrogen peroxide ($H_2O_2$).

In an embodiment, about 0.1 g of the baobab fruit fine powder can be added to the prepared detected acid mixture within a vessel to obtain a solution with the vessel.

In an embodiment, the vessel can be sealed and the solution can be heated to digest the baobab fruit fine powder in the solution within the sealed vessel in an oven cavity of a microwave digestion at about 100° C. for about 5 minutes, then at about 130° C. for about 15 minutes, and thereafter cooling the solution within the sealed vessel to obtain a digested baobab fruit fine powder in the solution within the sealed vessel.

In an embodiment, the digested baobab fruit fine powder can be filtered from the solution to obtain a filtered digested baobab fruit fine powder. Afterward, the filtered digested baobab fruit fine powder can be diluted with about 100 mL of deionized water to obtain a mixture.

In an embodiment, the plurality of chemical elements in the mixture can be measured using inductively coupled plasma mass spectrometry (ICP-MS). The plurality of chemical elements can be selected from the group consisting of sodium, magnesium, aluminum, potassium, calcium, vanadium, chromium, manganese, cobalt, copper, selenium, barium, other chemical elements, and combinations thereof.

In a further embodiment, the present subject matter relates to a method of determining accuracy of response surface methodology (Box-Behnken design), the method includes obtaining a baobab fruit; preparing an analyte solution; adding the analyte solution at various concentrations to the baobab fruit; and determining recovery rates (R) for each chemical elements in the baobab fruit.

In one embodiment, the method of determining accuracy of response surface methodology (Box-Behnken design) can include obtaining a baobab fruit which can be purchased from a local market and can be used as a home control sample.

In an embodiment, the analyte solution can be selected from the group consisting of barium, sodium, magnesium, aluminum, potassium, calcium, vanadium, chromium, manganese, cobalt, copper, zinc, iron, and selenium, other chemical elements, and combinations thereof.

In an embodiment, the analyte solution can be added at concentrations of about 25 ug/L, about 50 ug/L, and about 100 ug/L to the baobab fruit.

FIG. 1 shows the process for optimizing microwave digestion as described herein.

The following examples illustrate the present teachings.

EXAMPLES

Example 1

Measuring a Plurality of Chemical Elements in a Baobab Fruit Pulp

The process of measuring a plurality of chemical elements in a baobab fruit pulp was conducted using the following steps.

Preparation of pulp: Pulp from a baobab fruit was manually separated from the seed of the baobab fruit.

Homogenization: The baobab fruit pulp was crushed and homogenized using an agate mortar and pestle to obtain a homogenized baobab fruit pulp.

Sieving: The homogenized baobab fruit pulp was placed in a plastic sieve with 1 mm pores to obtain baobab fruit fine powder.

Preparation of acid mixtures: A plurality of acid mixtures were prepared. The plurality of acid mixtures were comprised of 12 acid mixtures each respectively comprising: a) about 3 mL of nitric acid ($HNO_3$), b) about 5 mL of $HNO_3$, c) about 7 mL of $HNO_3$, d) about 7 mL of $HNO_3$:water ($H_2O$) (1:3), e) about 7 mL of $HNO_3:H_2O$ (1:1), f) about 7 mL of $HNO_3:H_2O$ (3:1), g) about 7 mL of $HNO_3:H_2O$ (1:1):about 2 mL of hydrogen peroxide ($H_2O_2$), h) about 7 mL of $HNO_3:H_2O$ (1:1):about 4 mL of $H_2O_2$, i) about 7 mL of $HNO_3:H_2O$ (1:1):about 6 mL of $H_2O_2$, j) about 3 mL of $HNO_3$:about 4 mL of $H_2O_2$, k) about 5 mL of $HNO_3$:about 4 mL of $H_2O_2$, and l) about 7 mL of $HNO_3$:about 4 mL of $H_2O_2$ as shown in Table 1.

Preparation of solutions: About 0.4 g of the baobab fruit fine powder was added to each of the prepared plurality of acid mixtures within a plurality of vessels to obtain a plurality of solutions with the plurality of vessels.

Heating: Each of the plurality of vessels were sealed and the plurality of solutions were heated to digest the baobab fruit fine powder in each of the plurality of solutions within each of the sealed plurality of vessels in an oven cavity of a microwave digestion at about 100° C. for about 5 minutes, then at about 130° C. for about 15 minutes, and thereafter cooling each of the plurality of solutions within each of the sealed plurality of vessels to obtain a digested baobab fruit fine powder in each of the plurality of solutions within each of the sealed plurality of vessels.

Filtering: The digested baobab fruit fine powder was filtered from each of the plurality of solutions to obtain a plurality of filtered digested baobab fruit fine powders.

Preparation of a mixture: Each of the plurality of filtered digested baobab fruit fine powders were diluted with about 100 mL of deionized water to obtain a plurality of mixtures.

ICP-MS: The plurality of chemical elements in each of the plurality of mixtures were measured using inductively coupled plasma mass spectrometry (ICP-MS). The plurality of chemical elements are selected from the group consisting of sodium, magnesium, aluminum, potassium, calcium, vanadium, chromium, manganese, cobalt, copper, selenium, barium, other chemical elements, and combinations thereof.

TABLE 1

The volume and concentration of the combination of nitric acid and hydrogen peroxide were used.

| Acid mixture No. | $HNO_3$ ml | $H_2O_2$ ml |
|---|---|---|
| 1 | 3 ml conc. | 0 ml |
| 2 | 5 ml conc. | 0 ml |
| 3 | 7 ml conc. | 0 ml |
| 4 | 7 ml $HNO_3$:$H_2O$ (1:3) | 0 ml |
| 5 | 7 ml $HNO_3$:$H_2O$ (1:1) | 0 ml |
| 6 | 7 ml $HNO_3$:$H_2O$ (3:1) | 0 ml |
| 7 | 7 ml $HNO_3$:$H_2O$ (1:1) | 2 ml |
| 8 | 7 ml $HNO_3$:$H_2O$ (1:1) | 4 ml |
| 9 | 7 ml $HNO_3$:$H_2O$ (1:1) | 6 ml |
| 10 | 3 ml conc. | 4 ml |
| 11 | 5 ml conc. | 4 ml |
| 12 | 7 ml conc. | 4 ml |

Example 2

Optimizing Microwave Digestion

The process of optimizing microwave digestion was conducted using the following steps.

Normalization: The measured plurality of chemical elements in each of the plurality of mixtures as mentioned in Example 1 were normalized to obtain a plurality of normalized measured chemical elements values as shown in Table 2. Normalization was conducted by dividing the chemical element concentration measured for each of the measured plurality of chemical elements in each of the plurality of mixtures by a highest concentration of the same chemical element measured for each of the measured plurality of chemical elements in each of the plurality of mixtures. As shown in Table 2, run No. 7, which corresponds to acid mixture No. 7 as shown in Table 1, generated chemical elements normalization values ranging from about 0.03 to about 1. This indicate that the acid mixture No. 7 has the greatest ability to extract all the chemical elements from the plurality of filtered digested baobab fruit pulp fine powders in comparison to all other acid mixtures shown in Table 1.

Response surface method methodology (Box-Behnken design): The plurality of normalized measured chemical elements values and microwave digestion factor variables were incorporated into a response surface methodology (Box-Behnken design) to generate a plurality of run data to obtain multiple response (MR) values and concentration values for each of the plurality of normalized measured chemical elements as shown in Table 3. The response surface methodology (Box-Behnken design) comprises about 27 factorial experiments with about 3 center points using a Minitab software. The microwave digestion factor variables comprise a microwave temperature of about 125° C., an acid mixture volume of about 10 mL, a sample weight of about 0.1 g, and a radiation time of about 15 minutes.

Determination and detection: Using the run data generated as shown in Table 3, it was determined which run data generated a highest multiple response value and highest concentration values for each of the plurality of normalized measured chemical elements. Afterward, a detection of which of the plurality of acid mixtures of as mentioned in Example 1 correspond with the determined run data was conducted to obtain optimized microwave digestion.

As shown in Table 3, run No. 7 produced the highest multiple response (MR) value with the highest element concentration values for aluminum (Al), manganese (Mn), copper (Cu), and selenium (Se), indicating conditions allowing for the determination of all chemical elements simultaneously. This run No. 7 corresponds to the acid mixture No. 7 (detected acid mixture) (about 7 mL of $HNO_3$:$H_2O$ (1:1): about 2 mL of hydrogen peroxide ($H_2O_2$)) as shown in Table 1.

TABLE 2

The normalization of each element and multiple responses (MR).

| | Normalization | | | | | | | | | | | | | | |
|---|---|---|---|---|---|---|---|---|---|---|---|---|---|---|---|
| Run Order | Na | Mg | Al | K | Ca | V | Cr µg/g | Mn | Fe | Co | Cu | Zn | Se | Ba | MR |
| 1 | 0.07 | 0.76 | 0.55 | 0.85 | 0.85 | 0.02 | 0.48 | 0.91 | 0.50 | 0.30 | 0.55 | 0.79 | 0.05 | 0.38 | 7.07 |
| 2 | 0.02 | 0.66 | 0.56 | 0.73 | 0.72 | 0.02 | 0.09 | 0.76 | 0.25 | 0.28 | 0.47 | 0.81 | 0.02 | 0.32 | 5.72 |
| 3 | 0.05 | 0.69 | 0.44 | 0.77 | 0.77 | 0.02 | 0.59 | 0.81 | 0.28 | 0.21 | 0.07 | 0.84 | 0.06 | 0.30 | 5.91 |
| 4 | 0.05 | 0.74 | 0.66 | 0.80 | 0.79 | 0.02 | 0.27 | 0.83 | 0.32 | 0.57 | 0.11 | 1.00 | 0.22 | 0.51 | 6.90 |
| 5 | 0.54 | 0.84 | 0.48 | 0.88 | 0.95 | 0.03 | 0.96 | 0.96 | 0.57 | 0.53 | 0.94 | 0.85 | 0.04 | 1.00 | 9.58 |
| 6 | 0.21 | 0.81 | 0.51 | 0.85 | 0.87 | 0.05 | 0.45 | 0.89 | 0.35 | 0.29 | 0.57 | 0.80 | 0.08 | 0.40 | 7.13 |
| 7 | 0.47 | 0.87 | 1.00 | 0.90 | 0.98 | 0.03 | 1.00 | 1.00 | 0.74 | 0.23 | 1.00 | 0.95 | 1.00 | 0.47 | 10.64 |
| 8 | 0.12 | 0.87 | 0.61 | 0.88 | 0.88 | 0.03 | 0.19 | 0.91 | 0.35 | 0.40 | 0.64 | 0.85 | 0.18 | 0.41 | 7.32 |
| 9 | 0.22 | 0.85 | 0.45 | 0.90 | 0.92 | 0.03 | 0.64 | 0.93 | 0.40 | 0.25 | 0.55 | 0.77 | 0.25 | 0.46 | 7.61 |
| 10 | 0.30 | 0.88 | 0.72 | 0.95 | 0.97 | 0.03 | 0.29 | 0.99 | 0.48 | 0.31 | 0.57 | 0.84 | 0.48 | 0.37 | 8.17 |
| 11 | 0.26 | 0.89 | 0.49 | 0.88 | 0.91 | 0.02 | 0.57 | 0.92 | 0.39 | 0.20 | 0.16 | 0.75 | 0.08 | 0.36 | 6.89 |
| 12 | 0.28 | 0.90 | 0.50 | 0.85 | 0.88 | 0.02 | 0.95 | 0.89 | 0.46 | 0.23 | 0.62 | 0.76 | 0.50 | 0.43 | 8.26 |
| 13 | 0.85 | 0.96 | 0.74 | 0.91 | 0.95 | 0.01 | 0.59 | 0.91 | 0.86 | 0.26 | 0.78 | 0.70 | 0.74 | 0.42 | 9.69 |
| 14 | 0.56 | 1.00 | 0.73 | 1.00 | 1.00 | 0.01 | 0.63 | 0.97 | 0.79 | 0.01 | 0.56 | 0.65 | 0.58 | 0.43 | 8.94 |
| 15 | 0.05 | 0.95 | 0.77 | 0.84 | 0.83 | 0.08 | 0.17 | 0.86 | 0.36 | 0.22 | 0.58 | 0.71 | 0.08 | 0.50 | 7.01 |

TABLE 2-continued

The normalization of each element and multiple responses (MR).

Normalization

| Run Order | Na | Mg | Al | K | Ca | V | Cr µg/g | Mn | Fe | Co | Cu | Zn | Se | Ba | MR |
|---|---|---|---|---|---|---|---|---|---|---|---|---|---|---|---|
| 16 | 0.08 | 0.92 | 0.76 | 0.80 | 0.79 | 0.02 | 0.09 | 0.82 | 0.40 | 0.19 | 0.29 | 0.67 | 0.18 | 0.41 | 6.44 |
| 17 | 1.00 | 0.96 | 0.34 | 0.87 | 0.94 | 0.02 | 1.00 | 0.89 | 1.00 | 0.27 | 0.71 | 0.70 | 0.43 | 0.39 | 9.52 |
| 18 | 0.28 | 0.86 | 0.75 | 0.74 | 0.78 | 0.02 | 0.60 | 0.78 | 0.92 | 0.32 | 0.73 | 0.74 | 0.38 | 0.36 | 8.27 |
| 19 | 0.08 | 0.95 | 0.59 | 0.75 | 0.76 | 0.02 | 0.28 | 0.79 | 0.36 | 0.25 | 0.59 | 0.66 | 0.31 | 0.37 | 6.75 |
| 20 | 0.07 | 0.85 | 0.77 | 0.67 | 0.66 | 0.03 | 0.09 | 0.68 | 0.35 | 0.21 | 0.52 | 0.58 | 0.26 | 0.38 | 6.13 |
| 21 | 0.14 | 0.94 | 0.78 | 0.78 | 0.78 | 0.02 | 0.29 | 0.82 | 0.48 | 0.29 | 0.67 | 0.70 | 0.09 | 0.38 | 7.14 |
| 22 | 0.07 | 0.88 | 0.65 | 0.73 | 0.71 | 0.01 | 0.28 | 0.74 | 0.40 | 0.09 | 0.13 | 0.55 | 0.30 | 0.36 | 5.91 |
| 23 | 0.25 | 0.93 | 0.79 | 0.79 | 0.78 | 1.00 | 0.23 | 0.83 | 0.52 | 0.23 | 0.85 | 0.74 | 0.09 | 0.40 | 8.42 |
| 24 | 0.15 | 0.94 | 0.78 | 0.75 | 0.72 | 0.03 | 0.06 | 0.78 | 0.42 | 1.00 | 0.28 | 0.64 | 0.41 | 0.39 | 7.35 |
| 25 | 0.20 | 0.94 | 0.92 | 0.72 | 0.71 | 0.02 | 0.10 | 0.76 | 0.47 | 0.20 | 0.58 | 0.59 | 0.32 | 0.37 | 6.90 |
| 26 | 0.18 | 0.89 | 0.63 | 0.69 | 0.68 | 0.02 | 0.13 | 0.72 | 0.44 | 0.17 | 0.57 | 0.54 | 0.31 | 0.45 | 6.42 |
| 27 | 0.19 | 0.62 | 1.00 | 0.48 | 0.50 | 0.03 | 0.33 | 0.57 | 0.92 | 0.86 | 0.71 | 0.51 | 0.36 | 0.31 | 7.37 |

TABLE 3

Multiple responses (MR) and chemical element concentrations during Box-Behnken design digesting experiments.

| Run Order | 23 Na µg/g | 24 Mg mg/g | 27 Al µg/g | 39 K mg/g | 7 Ca mg/g | 51 V µg/g | 52 Cr µg/g | 55 Ma µg/g | 56 Fe µg/g | 59 Co µg/g | 63 Cu µg/g | 66 Za µg/g | 78 Se µg/g | 137 Ba µg/g | MR |
|---|---|---|---|---|---|---|---|---|---|---|---|---|---|---|---|
| 1 | 13.270 | 1.515 | 19.457 | 14.829 | 1.862 | 0.036 | 0.352 | 7.119 | 36.347 | 0.1 | 9.154 | 0.909 | 0.0301 | 16.909 | 7.070 |
| 2 | 3.513 | 1.311 | 19.941 | 12.757 | 1.573 | 0.04 | 0.069 | 5.945 | 18.224 | 0.092 | 7.784 | 0.938 | 0.0137 | 14.158 | 5.721 |
| 3 | 9.824 | 1.381 | 15.359 | 13.448 | 1.681 | 0.036 | 0.434 | 6.319 | 20.554 | 0.069 | 1.122 | 0.974 | 0.0383 | 13.204 | 5.907 |
| 4 | 9.636 | 1.472 | 23.256 | 13.873 | 1.722 | 0.039 | 0.199 | 6.447 | 23.467 | 0.19 | 1.892 | 1.155 | 0.134 | 22.730 | 6.895 |
| 5 | 96.978 | 1.667 | 17.079 | 15.254 | 2.091 | 0.055 | 0.703 | 7.468 | 41.520 | 0.178 | 15.512 | 0.986 | 0.0242 | 44.619 | 9.578 |
| 6 | 38.217 | 1.622 | 18.043 | 14.796 | 1.896 | 0.087 | 0.328 | 6.936 | 25.341 | 0.097 | 9.394 | 0.926 | 0.0475 | 17.905 | 7.130 |
| 7 | 83.953 | 1.728 | 35.300 | 15.662 | 2.155 | 0.059 | 0.728 | 7.799 | 54.186 | 0.077 | 16.524 | 1.098 | 0.5956 | 20.788 | 10.637 |
| 8 | 22.173 | 1.742 | 21.505 | 15.267 | 1.932 | 0.047 | 0.137 | 7.094 | 25.895 | 0.132 | 10.61 | 0.984 | 0.1067 | 18.136 | 7.319 |
| 9 | 38.554 | 1.693 | 15.837 | 15.717 | 2.008 | 0.044 | 0.468 | 7.287 | 29.036 | 0.083 | 9.024 | 0.892 | 0.148 | 20.665 | 7.608 |
| 10 | 53.261 | 1.756 | 25.256 | 16.554 | 2.115 | 0.049 | 0.213 | 7.693 | 35.264 | 0.102 | 9.476 | 0.965 | 0.2877 | 16.725 | 8.171 |
| 11 | 46.161 | 1.785 | 17.437 | 15.387 | 1.988 | 0.036 | 0.414 | 7.163 | 28.627 | 0.067 | 2.718 | 0.864 | 0.0493 | 16.187 | 6.894 |
| 12 | 51.030 | 1.788 | 17.554 | 14.713 | 1.925 | 0.037 | 0.696 | 6.923 | 33.665 | 0.077 | 10.176 | 0.876 | 0.2982 | 19.206 | 8.260 |
| 13 | 152.853 | 1.92 | 26.223 | 15.846 | 2.078 | 0.023 | 0.431 | 7.12 | 62.766 | 0.088 | 12.956 | 0.804 | 0.4397 | 18.752 | 9.694 |
| 14 | 101.035 | 1.996 | 25.827 | 17.403 | 2.19 | 0.023 | 0.462 | 7.561 | 58.078 | 0.004 | 9.242 | 0.755 | 0.3447 | 19.219 | 8.939 |
| 15 | 8.091 | 1.902 | 27.343 | 14.636 | 1.816 | 0.133 | 0.127 | 6.703 | 26.131 | 0.074 | 9.574 | 0.816 | 0.0493 | 22.502 | 7.005 |
| 16 | 15.198 | 1.842 | 26.990 | 13.996 | 1.737 | 0.04 | 0.069 | 6.37 | 28.923 | 0.063 | 4.792 | 0.770 | 0.1101 | 18.418 | 6.443 |
| 17 | 179.261 | 1.916 | 12.094 | 15.213 | 2.051 | 0.03 | 0.731 | 6.931 | 73.074 | 0.091 | 11.676 | 0.804 | 0.2542 | 17.552 | 9.515 |
| 18 | 50.777 | 1.724 | 26.491 | 12.956 | 1.707 | 0.032 | 0.442 | 6.095 | 66.935 | 0.108 | 12.018 | 0.858 | 0.2269 | 15.943 | 8.275 |
| 19 | 13.743 | 1.892 | 20.778 | 13.135 | 1.667 | 0.033 | 0.203 | 6.172 | 26.073 | 0.082 | 9.774 | 0.763 | 0.1851 | 16.530 | 6.754 |
| 20 | 12.914 | 1.699 | 27.208 | 11.647 | 1.449 | 0.046 | 0.069 | 5.316 | 25.620 | 0.071 | 8.606 | 0.671 | 0.1558 | 16.763 | 6.130 |
| 21 | 24.429 | 1.871 | 27.433 | 13.588 | 1.711 | 0.034 | 0.211 | 6.362 | 35.055 | 0.097 | 11.082 | 0.803 | 0.0516 | 17.04 | 7.142 |
| 22 | 13.285 | 1.757 | 22.853 | 12.734 | 1.557 | 0.018 | 0.204 | 5.753 | 29.573 | 0.03 | 2.178 | 0.639 | 0.1804 | 15.873 | 5.910 |
| 23 | 44.270 | 1.854 | 27.731 | 13.703 | 1.716 | 1.744 | 0.17 | 6.451 | 37.800 | 0.075 | 14.002 | 0.858 | 0.0546 | 18.028 | 8.421 |
| 24 | 26.262 | 1.883 | 27.451 | 12.984 | 1.576 | 0.045 | 0.046 | 6.071 | 31.050 | 0.333 | 4.702 | 0.738 | 0.2436 | 17.462 | 7.349 |
| 15 | 35.761 | 1.872 | 32.556 | 12.536 | 1.565 | 0.03 | 0.073 | 5.934 | 34.154 | 0.068 | 9.578 | 0.684 | 0.1884 | 16.531 | 6.903 |
| 26 | 32.937 | 1.77 | 22.315 | 11.954 | 1.493 | 0.028 | 0.092 | 5.634 | 32.469 | 0.058 | 9.338 | 0.629 | 0.1832 | 20.020 | 6.420 |
| 27 | 33.950 | 1.242 | 35.264 | 8.389 | 1.09 | 0.047 | 0.239 | 4.424 | 66.863 | 0.285 | 11.744 | 0.589 | 0.2131 | 13.955 | 7.374 |

Example 3

Microwave Digestion

The process of performing microwave digestion was conducted using the following steps.

Preparation of pulp: Pulp from a baobab fruit was manually separated from the seed of the baobab fruit.

Homogenization: The baobab fruit pulp was crushed and homogenized using an agate mortar and pestle to obtain a homogenized baobab fruit pulp.

Sieving: The homogenized baobab fruit pulp was placed in a plastic sieve with 1 mm pores to obtain baobab fruit fine powder.

Preparation of acid mixture: The detected acid mixture as mentioned in Example 2 was prepared. The detected acid mixture comprises about 7 mL of $HNO_3:H_2O$ (1:1):about 2 mL of hydrogen peroxide ($H_2O_2$) as shown in Table 1.

Preparation of solution: About 0.1 g of the baobab fruit fine powder was added to the prepared detected acid mixture within a vessel to obtain a solution within the vessel.

Heating: The vessel was sealed and the solution was heated to digest the baobab fruit fine powder in the solution within the sealed vessel in an oven cavity of a microwave digestion at about 100° C. for about 5 minutes, then at about 130° C. for about 15 minutes, and thereafter cooling the solution within the sealed vessel to obtain a digested baobab fruit fine powder in the solution within the sealed vessel.

Filtering: The digested baobab fruit fine powder was filtered from the solution to obtain a filtered digested baobab fruit fine powder.

Preparation of a mixture: The filtered digested baobab fruit fine powder was diluted with about 100 mL of deionized water to obtain a mixture.

ICP-MS: The plurality of chemical elements in the mixture were measured using inductively coupled plasma mass spectrometry (ICP-MS). The plurality of chemical elements is selected from the group consisting of sodium, magnesium, aluminum, potassium, calcium, vanadium, chromium, manganese, cobalt, copper, selenium, barium, other chemical elements, and combinations thereof.

Example 4

Determining the Accuracy of the Response Surface Methodology (Box-Behnken Design)

The process of determining accuracy of the response surface methodology (Box-Behnken design) was conducted using the following steps.

Baobab fruit: A baobab fruit was obtained. The baobab fruit was purchased from a local market and used as a home control (CS) sample.

Preparation of an analyte solution: An analyte solution was prepared. The analyte solution is selected from the group consisting of barium, sodium, magnesium, aluminum, potassium, calcium, vanadium, chromium, manganese, cobalt, copper, zinc, iron, and selenium, other chemical elements, and combinations thereof.

Adding the analyte solution to the baobab fruit: The analyte solution was added at concentrations of about 25 ug/L, about 50 ug/L, and about 100 ug/L to the baobab fruit as shown in Table 4.

Recovery rates: Recovery rates (R) for each chemical elements in the baobab fruit were determined.

In order to determine the recovery rates (R) for each of the chemical elements, the following formula was used:

$$R = \frac{C_{obs} - C_{native}}{C_{spiked}} \times 100$$

Where $C_{obs}$ is the analyte solution concentration of a chemical element in the spiked sample. $C_{native}$ is the analyte solution concentration in an unspiked control sample. $C_{spiked}$ is the analyte solution concentration in the analyte solution added to the sample.

As shown in Table 4, the accuracy was established by calculating chemical element recoveries in control samples spiked with three known quantities (about 25 ug/L, about 50 ug/L, and about 100 ug/L) and 3 replicates for each level. Results varied from about 71.40±about 1.425 to about 108.95±about 0.459. The results confirmed the method's sensitivity for the simultaneous measurement of sodium (Na), magnesium (Mg), aluminum (Al), potassium (K), calcium (Ca), vanadium (V), chromium (Cr), manganese (Mn), iron (Fe), cobalt (Co), copper (Cu), zinc (Zn), selenium (Se), and barium (Ba) in the pulp of baobab fruit.

TABLE 4

The chemical elements recoveries of spiked samples occurred at three different concentrations (25 ug/L, 50 ug/L, and 100 ug/L).

| Element | Spike 1 (25 µg/L) ± RSD | Spike 2 (50 µg/L) ± RSD | Spike 3 (100 µg/L) ± RSD |
| --- | --- | --- | --- |
| Na | 90.79 ± 1.308 | 94.90 ± 0.090 | 98.52 ± 0.602 |
| Mg | 93.20 ± 1.299 | 101.67 ± 0.712 | 101.16 ± 0.262 |
| Al | 90.62 ± 1.309 | 92.21 ± 1.387 | 97.16 ± 3.960 |
| K | 103.03 ± 1.299 | 99.42 ± 0.060 | 98.67 ± 0.098 |
| Ca | 71.40 ± 1.425 | 108.95 ± 0.459 | 101.04 ± 0.225 |
| V | 86.65 ± 1.366 | 86.46 ± 0.002 | 86.93 ± 0.001 |
| Cr | 86.14 ± 0.323 | 85.82 ± 0.004 | 86.81 ± 0.014 |
| Mn | 84.05 ± 1.419 | 84.35 ± 0.018 | 84.42 ± 0.010 |
| Fe | 99.51 ± 1.319 | 84.30 ± 0.023 | 81.76 ± 0.013 |
| Co | 84.91 ± 1.407 | 84.80 ± 0.011 | 86.15 ± 0.019 |
| Cu | 99.39 ± 1.299 | 90.86 ± 0.014 | 86.62 ± 0.017 |
| Zn | 84.57 ± 1.442 | 87.77 ± 0.003 | 86.32 ± 0.018 |
| Se | 98.06 ± 1.333 | 77.09 ± 0.027 | 81.37 ± 0.006 |
| Ba | 90.60 ± 1.299 | 90.59 ± 0.046 | 91.47 ± 0.153 |

Example 5

ICH Principles

Using ICH principles (International Council for Harmonization of Technical Requirements for Pharmaceuticals for Human Use), a calibration linearity, accuracy, precision, limits of detection (LOD), and limits of quantification (LOQ) validation features of each chemical element's analytical method were evaluated. The chemical element calibration curves were drawn over the concentration ranges of about 0.01 ug/L to about 150 ug/L, and the linearity of the calibration curves were demonstrated by the correlation coefficients ($R^2$). The correlation coefficients ($R^2$) ranged between about 0.9947 and about 1.00 as shown in Table 5. Also, repeatability values were calculated as relative standard deviation (RSD) from the examination of three sample analyte solutions digested on the same day using the same procedure. The relative standard deviation (RSD) values were about ≤7.1587 as shown in Table 5.

The LOD and LOQ of each chemical elements were found to be about 3 and about 10 standard deviations, respectively, above the slope of the calibration curve. The LOD and LOQ values as shown in Table 5 ranged from about 0.0003 ng/L to about 0.7920 ng/L and from about 0.0011 ng/L to about 2.6400 ng/L, respectively.

TABLE 5

Mass, correlation coefficients (R2), limits of detection (LOD), limits of quantification (LOQ), and repeatability (RSD) for determining chemical elements in the pulp of baobab fruit.

| Name | Mass | $R^2$ | LOD ng/L | LOQ ng/L | Repeatability (RSD) |
| --- | --- | --- | --- | --- | --- |
| Na | 23 | 0.9970 | 0.0037 | 0.0123 | 5.5008 |
| Mg | 24 | 0.9991 | 0.0030 | 0.0098 | 6.6120 |
| Al | 27 | 0.9991 | 0.0080 | 0.0268 | 3.2212 |
| K | 39 | 0.9978 | 0.0413 | 0.1375 | 1.8535 |
| Ca | 44 | 0.9985 | 0.5007 | 1.6689 | 3.1306 |
| V | 51 | 0.9993 | 0.0010 | 0.0033 | 2.6660 |
| Cr | 52 | 0.9993 | 0.0168 | 0.0560 | 2.0996 |
| Mn | 55 | 0.9994 | 0.0067 | 0.0225 | 0.8059 |
| Fe | 56 | 0.9947 | 0.0405 | 0.1350 | 3.7684 |
| Co | 59 | 0.9993 | 0.0003 | 0.0011 | 2.8272 |
| Cu | 63 | 1.0000 | 0.7920 | 2.6400 | 7.1587 |
| Zn | 66 | 0.9997 | 0.4061 | 1.3537 | 4.7788 |
| Se | 78 | 0.9988 | 0.4461 | 1.4871 | 2.1687 |
| Ba | 137 | 0.9999 | 0.0064 | 0.0213 | 2.7410 |

We claim:

1. A method of measuring a plurality of chemical elements in a baobab fruit pulp, the method comprising:
   obtaining pulp from a baobab fruit;
   crushing and homogenizing the baobab fruit pulp to obtain a homogenized baobab fruit pulp;
   sieving the homogenized baobab fruit pulp to obtain baobab fruit fine powder;
   preparing a plurality of acid mixtures, wherein the plurality of acid mixtures comprise acid mixtures that consist of only nitric acid and acid mixtures that consist of nitric acid and one or more of water and hydrogen peroxide;
   adding the baobab fruit fine powder to each of the prepared plurality of acid mixtures to obtain a plurality of solutions;
   heating each of the plurality of solutions in an oven cavity of a microwave to digest the baobab fruit fine powder in each of the plurality of solutions to obtain a digested baobab fruit fine powder in each of the plurality of solutions;
   cooling the plurality of solutions;
   filtering the digested baobab fruit fine powder from each of the plurality of solutions to obtain a plurality of filtered digested baobab fruit fine powders;
   diluting each of the plurality of filtered digested baobab fruit fine powders with water to obtain a plurality of mixtures; and
   measuring the plurality of chemical elements in each of the plurality of mixtures to obtain an optimized mixture for digestion of baobab fruit fine powder using inductively coupled plasma mass spectrometry (ICP-MS), wherein the plurality of chemical elements are selected from the group consisting of sodium, magnesium, aluminum, potassium, calcium, vanadium, chromium, manganese, cobalt, copper, selenium, barium, and combinations thereof.

2. The method of claim 1, wherein the homogenized baobab fruit pulp is prepared by crushing and homogenizing the baobab fruit pulp with an agate mortar and pestle.

3. The method of claim 1, wherein the plurality of acid mixtures are comprised of 12 acid mixtures comprising:
   a) about 3 mL of nitric acid ($HNO_3$),
   b) about 5 mL of $HNO_3$,
   c) about 7 mL of $HNO_3$,
   d) about 7 mL of $HNO_3$:water ($H_2O$) (1:3),
   e) about 7 mL of $HNO_3$:$H_2O$ (1:1),
   f) about 7 mL of $HNO_3$:$H_2O$ (3:1),
   g) about 7 mL of $HNO_3$:$H_2O$ (1:1):about 2 mL of hydrogen peroxide ($H_2O_2$),
   h) about 7 mL of $HNO_3$:$H_2O$ (1:1):about 4 mL of $H_2O_2$,
   i) about 7 mL of $HNO_3$:$H_2O$ (1:1):about 6 mL of $H_2O_2$,
   j) about 3 mL of $HNO_3$:about 4 mL of $H_2O_2$,
   k) about 5 mL of $HNO_3$:about 4 mL of $H_2O_2$, and
   l) about 7 mL of $HNO_3$:about 4 mL of $H_2O_2$.

4. The method of claim 3, wherein the plurality of solutions are prepared by adding about 0.4 g of the baobab fruit fine powder to each of the prepared plurality of acid mixtures within a plurality of vessels.

5. The method of claim 4, wherein the digested baobab fruit fine powder in each of the plurality of solutions within each of the plurality of vessels are prepared by sealing each of the plurality of vessels and heating the plurality of solutions to digest the baobab fruit fine powder in each of the plurality of solutions within each of the sealed plurality of vessels in the oven cavity of the microwave at about 100° C. for about 5 minutes, then at about 130° C. for about 15 minutes, and thereafter cooling each of the plurality of solutions within each of the sealed plurality of vessels.

6. A method of optimizing microwave digestion, the method comprising:
   normalizing the measured plurality of chemical elements in each of the plurality of mixtures of claim 1 to obtain a plurality of normalized measured chemical elements values;
   generating a plurality of run data by incorporating the plurality of normalized measured chemical elements values and microwave digestion factor variables into a response surface methodology using a Box-Behnken design to obtain multiple response (MR) values and concentration values for each of the plurality of normalized measured chemical elements;
   determining which run data generated a highest multiple response value and highest concentration values for each of the plurality of normalized measured chemical elements;
   and detecting which of the plurality of acid mixtures of claim 1 correspond with the determined run data to obtain optimized microwave digestion,
   wherein each of the plurality of normalized measured chemical elements values are prepared by dividing concentration values measured for each of the measured plurality of chemical elements in each of the plurality of mixtures by a highest concentration of the same chemical element measured for each of the measured plurality of chemical elements in each of the plurality of mixtures, and
   wherein the multiple response values and concentration values for each of the plurality of normalized measured chemical elements are prepared by generating a plurality of run data by incorporating the plurality of normalized measured chemical elements values and microwave digestion factor variables into the response surface methodology using the Box-Behnken design comprising about 27 factorial experiments with about 3 center points.

7. The method of claim 6, wherein the microwave digestion factor variables comprise a microwave temperature of about 125° C., an acid mixture volume of about 10 mL, a sample weight of about 0.1 g, and a radiation time of about 15 minutes.

8. A method of performing microwave digestion, the method comprising:
   normalizing the measured plurality of chemical elements in each of the plurality of mixtures of claim 1 to obtain a plurality of normalized measured chemical elements values;
   generating a plurality of run data by incorporating the plurality of normalized measured chemical elements values and microwave digestion factor variables into a response surface methodology using a to obtain multiple response (MR) values and concentration values for the plurality of normalized measured chemical elements;

determining which run data generated a highest multiple response value and highest concentration values for each of the plurality of normalized measured chemical elements; and detecting which of the plurality of acid mixtures of claim 1 correspond with the determined run data to obtain optimized microwave digestion;

wherein the multiple response values and concentration values for the plurality of normalized measured chemical elements are prepared by generating a plurality of run data by incorporating the plurality of normalized measured chemical elements values and microwave digestion factor variables into the response surface methodology using the Box-Behnken design comprising about 27 factorial experiments with about 3 center points, and wherein the microwave digestion factor variables comprise a microwave temperature of about 125° C., an acid mixture volume of about 10 ml, a sample weight of about 0.1 g, and a radiation time of about 15 minutes;

the method further comprising:

obtaining pulp from a baobab fruit;

crushing and homogenizing the baobab fruit pulp to obtain a homogenized baobab fruit pulp;

sieving the homogenized baobab fruit pulp to obtain baobab fruit fine powder;

preparing the detected acid mixture;

adding the baobab fruit fine powder to the detected acid mixture to obtain a solution;

heating the solution to digest the baobab fruit fine powder in the solution to obtain a digested baobab fruit fine powder in the solution;

cooling the solution;

filtering the digested baobab fruit fine powder from the solution to obtain a filtered digested baobab fruit fine powder;

diluting the filtered digested baobab fruit fine powder with water to obtain a mixture; and measuring the mixture using inductively coupled plasma mass spectrometry (ICP-MS).

9. The method of claim 8, wherein the detected acid mixture comprises about 7 mL of $HNO_3:H_2O$ (1:1):about 2 mL of hydrogen peroxide ($H_2O_2$).

10. The method of claim 9, wherein the solution is prepared by adding about 0.1 g of the baobab fruit fine powder to the prepared detected acid mixture within a vessel.

11. The method of claim 10, wherein the digested baobab fruit fine powder in the solution within the vessel is prepared by sealing the vessel and heating the solution to digest the baobab fruit fine powder in the solution within the sealed vessel in an oven cavity of a microwave at about 100° C. for about 5 minutes then at about 130° C. for about 15 minutes and thereafter cooling the solution within the sealed vessel.

12. The method of claim 8, wherein the plurality of chemical elements are selected from the group consisting of sodium, magnesium, aluminum, potassium, calcium, vanadium, chromium, manganese, cobalt, copper, selenium, barium, and combinations thereof.

13. The method of claim 8, wherein the water comprises deionized water.

14. The method of claim 8, wherein the plurality of normalized measured chemical elements values are prepared by dividing a chemical element concentration measured for each of the measured plurality of chemical elements in each of the plurality of mixtures by a highest concentration of the same chemical element measured for each of the measured plurality of chemical elements in each of the plurality of mixtures.

* * * * *